United States Patent
Solà Carandell et al.

(10) Patent No.: US 9,533,994 B2
(45) Date of Patent: Jan. 3, 2017

(54) MONOCLINIC CRYSTALLINE FORM OF ASENAPINE MALEATE WITH A SPECIFIC PARTICLE SIZE DISTRIBUTION

(75) Inventors: Lluis Solà Carandell, Tarragona (ES); Jordi Cerón Bertran, Tarragona (ES); Glòria Freixas Pascual, Tarragona (ES); Pere Dalmases, Barcelona (ES)

(73) Assignee: Laboratorios Lesvi S.L., Barcelona (ES)

( * ) Notice: Subject to any disclaimer, the term of this patent is extended or adjusted under 35 U.S.C. 154(b) by 295 days.

(21) Appl. No.: 14/118,483

(22) PCT Filed: May 18, 2012

(86) PCT No.: PCT/GB2012/000449
§ 371 (c)(1),
(2), (4) Date: Jan. 21, 2014

(87) PCT Pub. No.: WO2012/156676
PCT Pub. Date: Nov. 22, 2012

(65) Prior Publication Data
US 2015/0336973 A1    Nov. 26, 2015

Related U.S. Application Data

(60) Provisional application No. 61/487,513, filed on May 18, 2011.

(51) Int. Cl.
*C07D 491/04* (2006.01)
*C07D 491/044* (2006.01)
*A61K 31/407* (2006.01)

(52) U.S. Cl.
CPC ......... *C07D 491/044* (2013.01); *A61K 31/407* (2013.01); *C07D 491/04* (2013.01); *C07B 2200/13* (2013.01); *Y10T 428/2982* (2015.01)

(58) Field of Classification Search
CPC .......................... C07D 491/04; C07D 491/044
See application file for complete search history.

(56) References Cited

FOREIGN PATENT DOCUMENTS

| WO | 2006106135 A1 | 10/2006 |
|---|---|---|
| WO | 2011159903 A2 | 12/2011 |
| WO | 2012038975 A2 | 3/2012 |
| WO | 2012066565 A2 | 5/2012 |

OTHER PUBLICATIONS

List of mental disorders [online], retrieved from the internet on Sep. 20, 2015. URL; https://en.wikipedia.org/wiki/List_of_mental_disorders.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http:llwww.cnn.com120031HEALTHlconditionslO91241alzheimers.drug.aplindexhtml>.*
Bipolar disorder [online]. Retrieved from the internet on Apr. 4, 2016. URL; http://www.nimh.nih.gov/health/topics/bipolar-disorder/index.shtml.*
European Patent Office, International Search Report, from corresponding International Application No. PCT/GB2012/000449, mailed Jul. 3, 2012.
Synthon BV. Crystallisation method for the monoclinic form of asenapine maleate, Research Disclosure, Mason Publications, Hampshire, GB, (2007) vol. 523, No. 12, 1093.
Funke CW, et al. Physico-Chemical Properties and Stability of Trans-5-Chloro-2-Methyl 2, 3, 3A, 12B-Tetrahydro-1H-Dibenz-2,3:6,70 Oxepino-4,5-C) Pyrrolidine Maleate, Arzneimittel Forschung. Drug Research, ECV Editio Cantor Verlag, Aulendorf, DE, (1990) vol. 40, No. 5, 536-539.

* cited by examiner

*Primary Examiner* — Shawquia Jackson
(74) *Attorney, Agent, or Firm* — Stites & Harbison, PLLC; Terry L. Wright (57) ABSTRACT

A monoclinic crystalline form of asenapine maleate is described, which is characterized in that it is not micronised and has a particle size distribution characterized by a d90 of 40 μm or less. A process for the preparation of a monoclinic crystalline form of asenapine maleate is also described, the process comprising the following steps: a) providing a mixture of monoclinic asenapine maleate and an organic solvent which, under the conditions of the process, acts as an antisolvent; b) stirring the mixture at a temperature between 15 and 60° C.; and c) collecting the crystals, wherein the organic solvent is selected from alcohols, ketones, ethers, esters, hydrocarbons or mixtures thereof.

16 Claims, 4 Drawing Sheets

MONOCLINIC CRYSTALLINE FORM OF ASENAPINE MALEATE WITH A SPECIFIC PARTICLE SIZE DISTRIBUTION

FIELD OF THE INVENTION

The present invention relates to a polymorphic form of a compound and a process for its preparation. In particular, the invention relates to a monoclinic crystalline form of asenapine maleate having low particle size, to a process for its preparation and to its use in medicine.

BACKGROUND OF THE INVENTION

Asenapine or trans-5-chloro-2-methyl-2,3,3a,12b-tetrahydro-1H-dibenz[2,3:6,7]oxepino[4,5-c]pyrrole, was first described in U.S. Pat. No. 4,145,434 by van der Burg and is represented by a structure of Formula 1:

1

Asenapine is a broad-spectrum, high potency serotonin, noradrenaline and dopamine antagonist, which exhibits potential antipsychotic activity. Asenapine is marketed as its maleate salt for the treatment of schizophrenia and manic episodes associated with bipolar I disorders, in the form of sublingual tablets under the trademark SAPHRIS.

Pharmaceutical compositions comprising asenapine maleate for sublingual or buccal administration were first described in EP 0 746 317 B1. These sublingual tablets were prepared by a freeze-drying (lyophilisation) process. This process involves freezing off an aqueous-based drug solution followed by sublimation of the ice in a vacuum, an unworkable method for industrial applications.

As described in Funke et al., Arzneim.-Forsch./Drug Res., 40:536-539 (1990), asenapine maleate (Form H) was the first known polymorphic form. Form H is a monoclinic crystalline form having a melting point in the range of 141° C. to 145° C. EP 1 710 245 B1 and EP 1 917 267 B1 described the discovery of a new form of asenapine maleate (Form L), which is an orthorhombic crystalline form having a melting point in the range of 138° C. to 142° C. EP 1 710 245 131 and EP 1 917 267 B1 mention the importance of asenapine particle size since asenapine commercial sublingual tablets are dissolved in the mouth. Thus, particles having a size distribution characterized by a d95 (95% volume of the particles are smaller than or equal to the indicated size) of about 100 μm or less, more preferably about 50 μm or less, and even more preferably about 30 μm or less, is desirable for sublingual formulations. According to EP 1 710 245 B1 and EP 1 917 267 B1, the outcome of the micronisation process used therein, and which is necessary to reduce the particle size of crystals, appeared to be unpredictable when crystals of monoclinic form of asenapine maleate were subjected to the micronisation process. Crystals of the orthorhombic form were found to be present in addition to the known monoclinic form in the starting material. The present inventors have also observed that micronisation of the crystals of the monoclinic form of asenapine maleate, prepared as disclosed in U.S. Pat. No. 4,145,434, were not stable and eventually evolved to the orthorhombic crystalline form. On the contrary, micronisation of the orthorhombic crystalline form of asenapine maleate disclosed in EP 1 710 245 B1 and EP 1 917 267 B1 reproducibly resulted in asenapine maleate of the orthorhombic crystalline form comprising particles having a size distribution characterized by a d95 of 30 μm or less. The preparation process of the orthorhombic form of asenapine maleate described in EP 1 710 245 B1 and EP 1 917 267 B1 comprised a very long crystallization step (between 42-72 hours), unlike the crystallization of monoclinic form of asenapine maleate (about 3 hours), which makes the preparation of orthorhombic crystalline form of asenapine maleate of low particle size an economically disadvantageous procedure.

In accordance with regulatory requirements of the U.S. and other countries, e.g. the FDA's Good Manufacturing Practice ("GMP") requirements, when preparing pharmaceutical compositions containing active ingredients for administration to mammals, there is a need to produce crystalline forms, or polymorphs, which are as pure and as stable as possible. Differences in the chemical and physical properties of polymorphic forms of an active ingredient such as melting point, chemical reactivity and apparent solubility can have a direct effect on the ability to process and/or manufacture the active ingredient and its pharmaceutical compositions, as well as on its stability, dissolution and bioavailability. Thus, a process that provides an unstable polymorphic form is not desirable.

Therefore, it is desirable to develop a feasible preparation method to produce polymorphically stable asenapine maleate of low particle size, such that it is suitable for the preparation of sublingual pharmaceutical compositions of asenapine maleate.

BRIEF DESCRIPTION OF THE INVENTION

The present invention relates to a monoclinic crystalline form of asenapine maleate having low particle size. Thus, a first aspect of the invention relates to a stable form of monoclinic asenapine maleate of low particle size, which avoids the need to use a micronisation process.

A second aspect of the invention provides a process for the preparation of the monoclinic crystalline form of asenapine maleate of low particle size.

A third aspect of the invention relates to the use of the monoclinic crystalline form of asenapine maleate of low particle size for the preparation of a pharmaceutical composition.

DETAILED DESCRIPTION OF THE INVENTION

The inventors have surprisingly found a form of monoclinic asenapine maleate of low particle size that shows appropriate physico-mechanical properties for its manipulation at industrial scale, and which avoids the undesirable use of a micronisation process. This form of monoclinic asenapine maleate also shows good stability, i.e. it is stable.

The monoclinic crystalline form of asenapine maleate of low particle size is characterized by a particle size, in terms of d90, of lower than conventional crystallized (non-micronised) monoclinic asenapine maleate. The lower particle size avoids the need for a later micronisation process. Therefore, the monoclinic crystalline form of asenapine maleate of low particle size can be used directly in the preparation of sublingual pharmaceutical compositions, rather than requiring further processing as with conventional crystallized monoclinic asenapine maleate.

The particle size distribution of the monoclinic crystalline form of asenapine maleate of the invention is characterized by a d90 of 40 µm or less, or preferably by a d90 of less than 40 µm. More preferably, the particle size distribution of the monoclinic crystalline form of asenapine maleate is characterized by a d90 of 35 µm or less, 31 µm or less, 26 µm or less, 21 µm or less, or 16 µm or less. The particle size distribution of the monoclinic crystalline form of asenapine maleate may be characterized by a d90 of less than 35 µm, less than 31 µm, less than 26 µm, less than 21 µm, or less than 16 µm.

In preferred embodiments, the asenapine maleate of the invention has a particle size distribution characterised by a d95 of 40 µm or less, preferably 35 µm or less, and more preferably 30 µm or less, 25 µm or less, or 20 µm or less. The asenapine maleate of the invention may have a particle size distribution characterised by a d95 of less than 40 µm, preferably less than 35 µm, and more preferably less than 30 µm, less than 25 µm, or less than 20 µm.

The term 'dx' as used herein means that x % of the particles in a composition (based on volume) have a diameter equal to or less than a specified d value, preferably less than a specified d value. Thus, a d90 of 100 µm means that 90% of the particles, by volume, have a diameter equal to or less than 100 µm, preferably less than 100 µm.

The lower particle size of the monoclinic crystalline form of asenapine maleate of the invention avoids the need for a later micronisation process. The term 'micronisation' as used herein refers to the process of reducing the average diameter of a solid material's particles. Usually, the term micronisation is used when the particles that are produced are only a few micrometers in diameter. Traditional micronisation techniques are based on the use of friction to reduce particle size. Such methods include milling and grinding. Reduction in particle size may also take place as a result of collision and impact. As a result of the crystal particles of the invention not being prepared by micronisation, the particle size distribution of the crystal particles of the invention may be different compared to micronised particles, and the morphological features of the particles may also be different compared to micronised particles.

The new monoclinic form of asenapine maleate of the present invention can also be characterised by having high polymorphic purity and stability over time, not evolving to another polymorphic form. The obtained polymorphically pure form of monoclinic asenapine maleate shows high polymorphic stability, preferably such that it has more than 95% by weight of the monoclinic form. This may be measured after 1 month of storage, preferably after 2 months, and more preferably after 3 months. During the storage period of 1, 2 or 3 months, a temperature of 25° C. or 40° C., and a relative humidity of 60% or 75%, may be used. The same results, i.e. that the monoclinic form of asenapine maleate of the present invention is polymorphically stable, were obtained if the samples were contained in transparent or opaque vacuum containers. In addition, stability tests conducted on crystals having a d90 of 40 µm or less (40, 37 and 29 µm) under ambient environmental conditions, 15-28° C. and atmospheric pressure, have demonstrated that the novel monoclinic crystalline form of asenapine maleate of the present invention remained polymorphically stable after 14 months, with no other polymorphic forms being detected. The same results were obtained if the samples were contained in transparent or opaque vacuum containers. In a preferred embodiment, more than 98% by weight of monoclinic form is present. Most preferably more than 99% by weight of the monoclinic form is present. Thus, the new stable monoclinic form of asenapine maleate of the invention contains 5% by weight or less of any other crystalline form (e.g. the orthorhombic form), preferably less than 2% by weight of any other crystalline form, most preferably less than 1% by weight of any other crystalline form The monoclinic and orthorhombic forms of asenapine maleate can be characterised, and thus distinguished, by the powder X-ray diffraction pattern (PXRD) of the asenapine maleate, as described in EP1710245.

The long term stability properties in different storage conditions of the stable monoclinic asenapine maleate of the invention are of significant advantage for industrial scale applications.

The term "container" as used herein refers to an article which is used to contain, handle, store, and/or transport the stable monoclinic form of asenapine maleate of the invention. The container may be in direct contact with the asenapine maleate or a pharmaceutical composition containing the asenapine maleate. The container is so designed that the contents may be removed in a manner appropriate to the intended use of the contained asenapine maleate or pharmaceutical composition. The material used for the containers described in the context of the present invention and used in the Examples thereof, may be any transparent or opaque material, which does not interact physically or chemically with the contents in a way that alters the quality of the asenapine maleate or pharmaceutical composition beyond the limits tolerated by official (e.g. USP or European Pharmacopeia) requirements. The contents of the container may be under ambient environmental conditions of pressure or subjected to vacuum (i.e. sub-atmospheric pressure) conditions.

The inventors have also found a process for preparing the novel monoclinic crystalline form of asenapine maleate of low particle size in a stable form and which does not require any additional processing steps or special equipment.

Thus, a second aspect of the invention relates to a process for the preparation of a monoclinic crystalline form of asenapine maleate having low particle size, said process comprising: mixing monoclinic asenapine maleate with an organic solvent which, under the conditions of the process, acts as an antisolvent and is selected from alcohols, ketones, ethers, esters, hydrocarbons or mixtures thereof; followed by stirring at a temperature of between 15 and 60° C.; and collecting the crystals.

The term "antisolvent" means that the monoclinic asenapine maleate is not fully soluble and does not fully dissolve in the solvent. This results in the monoclinic asenapine maleate forming a suspension of crystals in the organic solvent under the conditions of the process. Preferably, the monoclinic asenapine maleate crystals are, at most, only partially soluble in the solvent. More preferably, the monoclinic asenapine maleate crystals are substantially insoluble in the solvent. This means that less than 5%, less than 4%, less than 3%, less than 2%, or less than 1% of the monoclinic asenapine maleate dissolves in the solvent. Although the solvent may well act as an antisolvent outside the following ranges, the solvent should act as an antisolvent between 15 and 60° C., between 20 and 55° C. or between 25 and 50° C.

Preferably, the monoclinic asenapine maleate, when mixed with the organic solvent which acts as an antisolvent under the conditions of the process, is in the form of a slurry. The term 'slurry' means a suspension of monoclinic asenapine maleate crystals in the organic solvent.

In prior art processes, monoclinic asenapine maleate crystals are dissolved in boiling ethanol at about 78° C. to form an asenapine maleate solution. This does not happen in the process of the present invention in which a suspension of monoclinic asenapine maleate crystals is present throughout the process until the crystals are collected. In effect, the prior art processes are recrystallisation process, whereas the process of the present invention does not involve recrystallisation, i.e. the process of the present invention does not involve crystallising monoclinic asenapine maleate crystals out of solution.

Without wanting to be held to any particular theory, it is thought that the lack of full dissolution is responsible for the stability of the crystals produced by the process.

In view of the fact that the process of the invention does not involve recrystallisation, the yield of the process is relatively high. In other words, the amount of asenapine maleate that if lost, over the course of the process, is relatively low. In some embodiments, the process has a yield of 95% or more. In other embodiments, the process has a yield of 96% or more. In further embodiments, the process has a yield of 96% or more, 97% or more, 98% or more, or 99% or more.

As used herein, the term "collecting" comprises one or more of filtration, washing and drying steps, in order to obtain the resulting crystals.

Suitable organic solvents are selected from alcohols (such as isopropanol, butanol, ethanol), ketones (such as methyl ethyl ketone, methyl isobutyl ketone), ethers (such as diethoxymethane, methyl tert-butyl ether, diisopropyl ether), esters (such as ethyl acetate, isopropyl acetate), hydrocarbons (such as cyclohexane, n-heptane, toluene) or mixtures thereof. Preferably, the organic solvents are methyl tert-butyl ether, diisopropyl ether, methyl ethyl ketone, methyl isobutyl ketone, isopropyl acetate or toluene. In one embodiment, the organic solvent is an ether such as methyl tert-butyl ether or diisopropyl ether. In another embodiment, the organic solvent is an ether such as methyl tert-butyl ether, diisopropyl ether or toluene.

Initiation of the stirring step of the process is carried out when the monoclinic asenapine maleate crystals are in the form of a suspension of crystals. The stirring takes place at a temperature of between 15 and 60° C. In some embodiments, the stirring may take place at a temperature of between 20 and 55° C. or between 25 and 50° C. It will be appreciated that the characteristics of the solvent used, in particular its boiling point, will influence the stirring temperature chosen.

The stirring may take place for any suitable length of time in order to produce the monoclinic crystalline form of asenapine maleate having a low particle size. A suitable length of time will be apparent to one skilled in the art and can be tested by measuring the particle size distribution of the crystals. The mixture may be stirred for between 1 and 25 hours. In certain embodiments, the mixture is stirred for between 1 and 20 hours. In some embodiments, the mixture is stirred for between 1 and 10 hours. In other embodiments, the mixture may be stirred for between 1 and 9 hours, between 1 and 8 hours, between 1 and 7 hours, or between 2 and 6 hours. The stirring may be carried out with any suitable magnetic or mechanical stirrer at any suitable speed in order to produce the monoclinic crystalline form of asenapine maleate having a low particle size. Preferably, the stirrer is a mechanical stirrer. Suitable mechanical stirrers may be propeller, hydrofoil, versafoil, pitched blade turbine and anchor stirrers. Preferably the mechanical stirrer is an anchor stirrer since it generates a tangential flow and a more homogeneous stirring in the centre and near the walls of the reactor. A suitable stirrer speed is between 50 and 1000 revolutions per minute (rpm).

Figure 1:
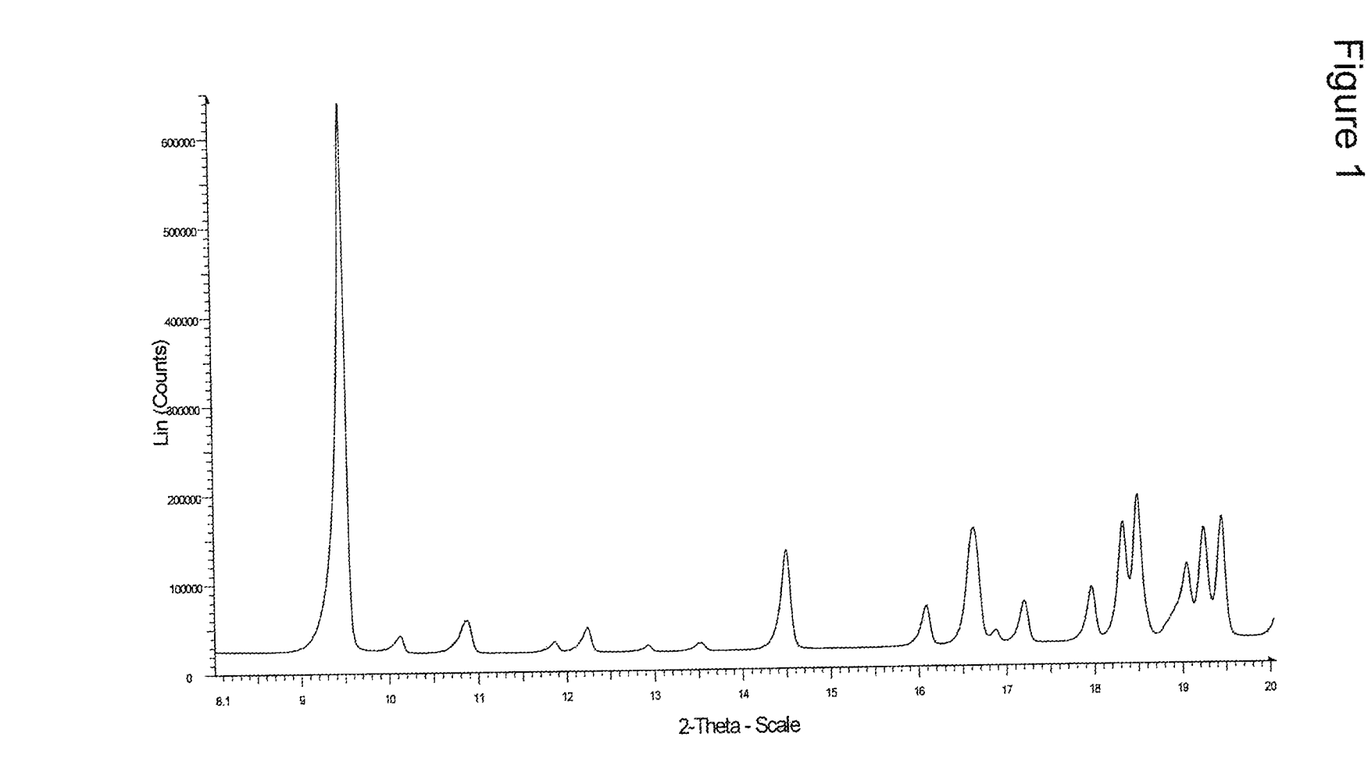
FIG. 1 shows a powder X-ray diffractogram for the monoclinic crystalline form of asenapine maleate of low particle size, obtained by way of Example 3.
Figure 2:
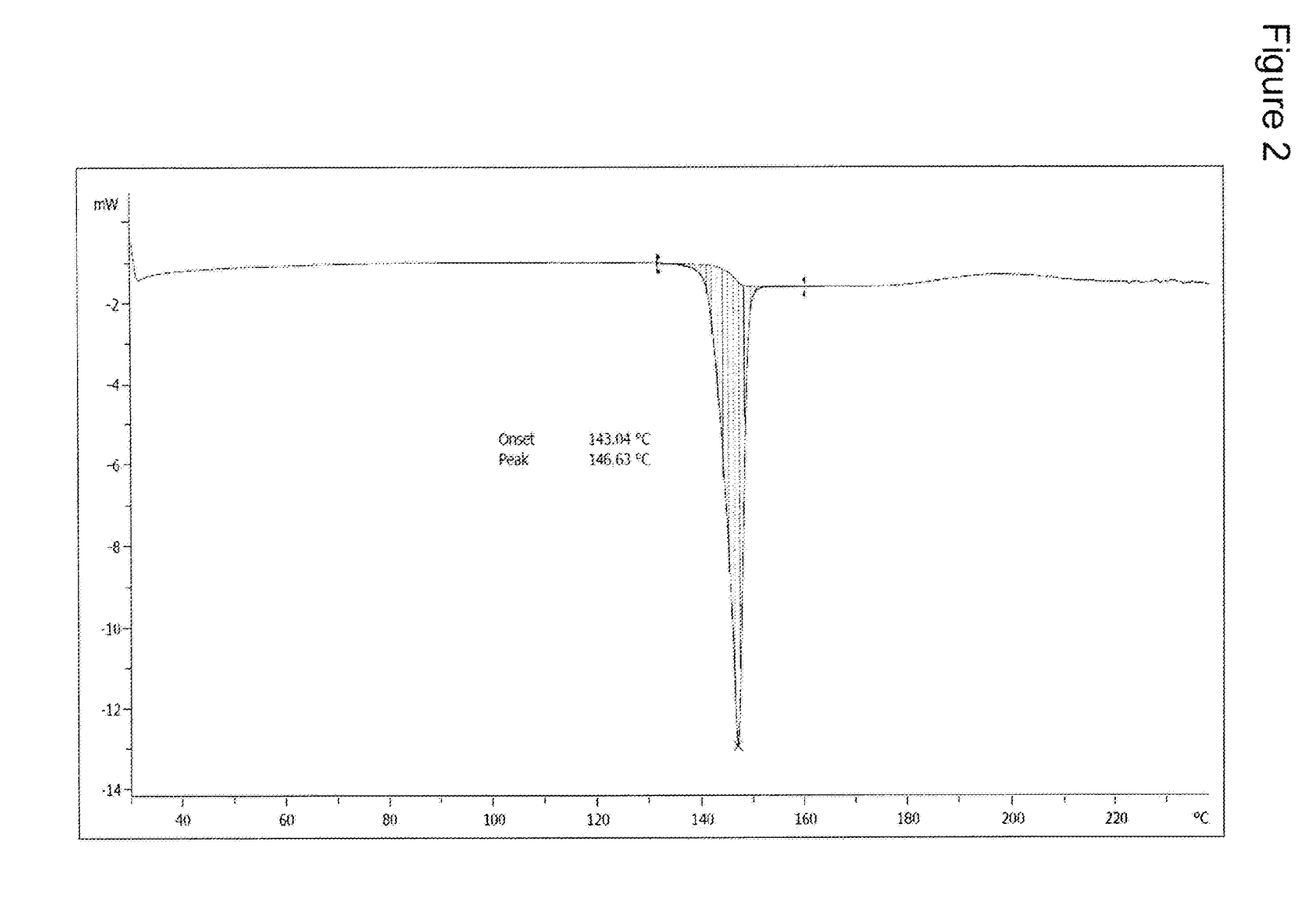
FIG. 2 shows the DSC analysis of the monoclinic crystalline form of asenapine maleate of low particle size, obtained by way of Example 3.
Figure 3:
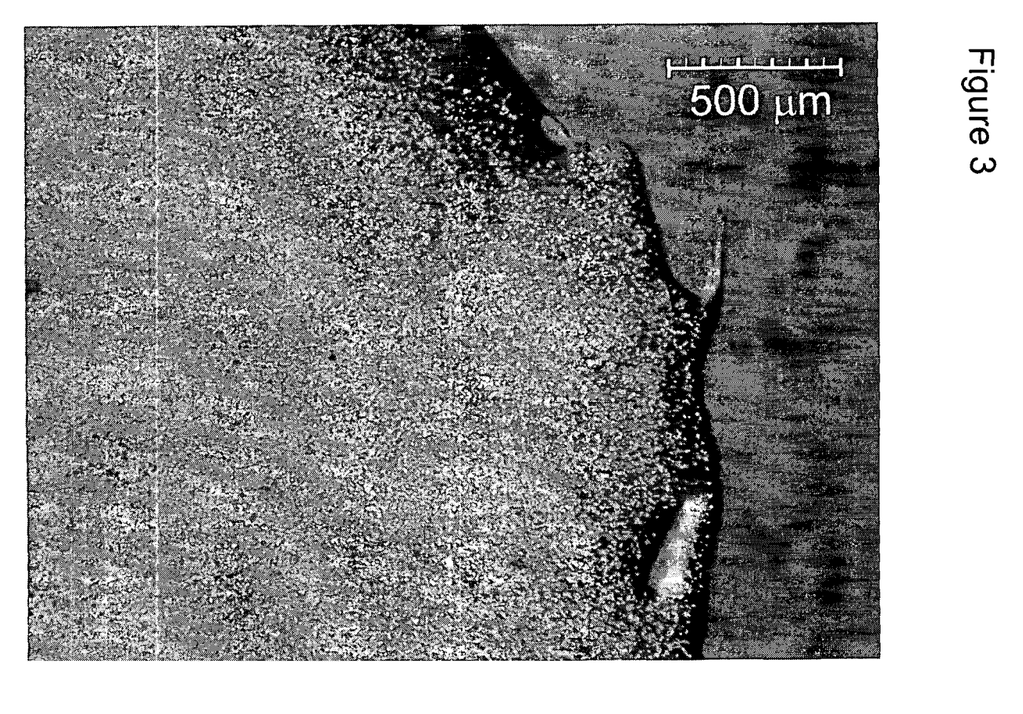
FIG. 3 shows a photograph of a sample of the monoclinic crystalline form of asenapine maleate of low particle size, obtained by way of Example 1.

The crystalline form of asenapine maleate of low particle size prepared according to the present invention is a particular polymorphic form, which has a melting point in the range of 142-147° C. that corresponds to the monoclinic form. The crystal structure of the monoclinic form of the present invention is characterized by being stable over time and not evolving to another polymorphic form. This monoclinic crystalline form of asenapine maleate is characterized, and thus distinguished from the orthorhombic form, by several analytical techniques known in the art such as X-ray powder diffraction patterns (XPRD) and differential scanning calorimetry (DSC) (FIG. 1 and FIG. 2).

In some embodiments, the particle size distribution of the monoclinic crystalline form of asenapine maleate produced by the process of the invention may be characterized by a d90 of 40 μm or less, preferably by a d90 of less than 40 μm. More preferably, the particle size distribution of the monoclinic crystalline form of asenapine maleate may be characterized by a d90 of 35 μm or less, 31 μm or less, 26 μm or less, 21 μm or less, or 16 μm or less. The particle size distribution of the monoclinic crystalline form of asenapine maleate may be characterized by a d90 of less than 35 μm, less than 31 μM, less than 26 μm, less than 21 μm, or less than 16 μm.

In preferred embodiments, the asenapine maleate produced by the process of the invention has a particle size distribution characterised by a d95 of 40 μm or less, preferably 35 μm or less, and more preferably 30 μm or less, 25 μm or less, or 20 μm or less. The asenapine maleate of the invention may have a particle size distribution characterised by a d95 of less than 40 μm, preferably less than 35 μm, and more preferably less than 30 μm, less than 25 μm, or less than 20 μm.

As discussed above, the process does not require micronisation in order to reduce the particle size of the crystals.

The monoclinic form of asenapine maleate produced by the process of the invention may also be characterised by having high polymorphic purity and stability over time, not evolving to another polymorphic form. This is discussed in more detail above.

The present invention also provides a monoclinic form of asenapine maleate, which is obtained or obtainable by the process of the present invention.

The monoclinic asenapine maleate subjected to the process of the present invention, may be prepared by crystallization of asenapine maleate in the presence of surfactants. The asenapine maleate, before crystallisation, may be a crude or amorphous or crystalline asenapine maleate. The surfactant used in this process may be added before or after the formation of the monoclinic crystals of asenapine maleate. In a preferred embodiment, the surfactant is added before the formation of the monoclinic crystals of asenapine maleate. The formation of asenapine maleate crystals according to this process comprises: dissolving a mixture of asenapine maleate and a surfactant in ethanol at reflux temperature; cooling the solution obtained to a temperature of between 10° C. and −10° C. under conditions of controlled cooling; optionally seeding the solution with asenapine maleate monoclinic crystals; and finally collecting the crystals of monoclinic asenapine maleate so obtained, i.e. those crystals which have crystallised from the solution.

In particular embodiments, the solution is cooled to a temperature of between 5° C. and −5° C. In other embodiments, the solution is cooled to a temperature of about 0° C.

When the solution is seeded with asenapine maleate monoclinic crystals, this seeding is preferably carried out when said solution is at a temperature of between 35° C. and 20° C. More preferably, the seeding is carried out when the solution is at a temperature of between 35° C. and 25° C. In some embodiments, the seeding is carried out when the solution is at a temperature of about 30° C.

As used herein, the term "surfactant" refers to a substance or substances which exhibit some surface or interfacial activity. Suitable surfactants are selected from non-ionic, anionic, cationic, amphoteric surfactants or mixtures thereof. Preferably, the surfactant is a non-ionic surfactant or a mixture of non-ionic surfactants. Non-limiting examples of non-ionic surfactants include saturated and/or unsaturated fatty acids having the structural formula $CH_3(CH_2)_m COOH$ where m is in the range of 6 to 18 (such as stearic acid, lauric acid, capric acid, myristic acid, caprylic acid, oleic acid) and their derivatives fatty alcohols (such as lauryl alcohol, cetyl alcohol, stearyl alcohol, capryl alcohol, cetyl stearyl alcohol, lauryl myristyl alcohol, oleyl alcohol), glyceryl esters including mono-, di- and tri-glycerides (such as glyceryl monostearate, glyceryl monolaurate), fatty acid esters of fatty alcohols and/or fatty acid esters of other alcohols including propylene glycol, polyethylene glycol (PEG), sorbitan, sucrose and cholesterol (such as PEG monolaureate, PEG monostearate, sorbitan monolaureate (also called Span 20), sorbitan monopalmitate (also called Span 40), sorbitan monooleate (also called Span 80), sorbitan monostearate (also called Span 60), sorbitan tristearate (also called Span 65), sorbitan trioleate (also called Span 85)); polyoxyethylene sorbitan fatty acid esters (such as polyoxyethylene 20 sorbitan monooleate (also called polysorbate 80 or Tween 80), polyoxyethylene 20 sorbitan monostearate (also called polysorbate 60 or Tween 60), polyoxyethylene 20 sorbitan monopalmitate (also called polysorbate 40 or Tween 40), polyoxyethylene 20 sorbitan monolaurate (also called polysorbate 20 or Tween 20)); polyoxyethylene glyceryl esters (such as polyoxyethylene glyceryl monostearate, polyoxyethylene glyceryl monooleate); polyoxyethylene castor oil derivatives (such as polyoxyl 40 hydrogenated castor oil (also called Cremophor RH 40), polyoxyl 35 castor oil (also called Cremophor EL), polyoxyl 60 hydrogenated castor oil (also called Cremophor RH 60)); polyoxyethylene steroidal esters; polyoxypropylene glyceryl esters; polyoxypropylene steroidal esters; polyoxyethylene ethers; polyglycol ethers; polyoxyethylene-polyoxypropylene copolimers (also called poloxamers or pluronics). Preferred non-ionic surfactants that can be used in the process include glyceryl esters including mono-, di- and tri-glycerides (such as glyceryl monostearate, glyceryl monolaurate), polyoxyethylene sorbitan fatty acid esters, polyoxyethylene castor oil derivatives or mixtures thereof. Preferably, the non-ionic surfactant is glyceryl monostearate, a Tween material such as Tween 80 or Tween 60, a Cremophor material such as Cremophor RH 40 or mixtures thereof.

In a preferred embodiment, the surfactant is added in an amount from 0.1% to 5% by weight relative to the weight of the asenapine maleate, preferably in an amount from 1% to 4% by weight relative to the weight of the asenapine maleate, more preferably from 2% to 3% and most preferably in amount of 2.5% by weight relative to the weight of the asenapine maleate.

The term "controlled cooling" as used herein means that the solution of asenapine maleate and surfactant is subjected to conditions which cause the refluxing temperature of the ethanol to fall at a controlled rate. The controlled rate may be a set number of degrees per minute. For example, the solution may be cooled at a rate of between 0.5° C. and 8° C. per minute. In certain embodiments, the solution may be cooled at a rate of between 0.5° C. and 5° C. per minute.

The solution may be cooled at different cooling rates under the conditions of controlled cooling. For example, the solution may be cool at a first rate until a particular temperature is reached and then at a second rate. In some embodiments, the solution is cooled at a rate of between 2° C. and 8° C. per minute until a temperature of between 5° C. and 15° C. is reached and then cooled at a rate of between 0.5° C. and 2° C. until a temperature of about 5° C. to −10° C. is reached. In other embodiments, the solution is cooled at a rate of between 2° C. and 5° C. per minute until a temperature of between 5° C. and 15° C. is reached and then cooled at a rate of between 0.5° C. and 2° C. until a temperature of about 5° C. to −5° C. is reached. In particular embodiments, the solution may be cooled at a rate of about 3° C. per minute until a temperature around 10° C. is reached; followed by a second controlled rate of around 1° C. per minute until a temperature around 0° C. is reached.

A third aspect of the invention relates to the stable and polymorphically pure form of monoclinic asenapine maleate of low particle size of the invention, in association with one or more pharmaceutically acceptable excipients or additives, in the form of a pharmaceutical composition. Such pharmaceutical composition may take the form of a dosage unit such as a tablet, capsule or a suppository. A preferred pharmaceutical composition is a tablet. Most preferably, the composition is a sublingual tablet.

A dosage unit of the invention, containing asenapine maleate and suitable for the treatment or prevention of mental disorders such as bipolar disorders, psychosis, or schizophrenia, may contain about 0.0005 to 500 mg of the stable and polymorphically pure form of monoclinic asenapine maleate of the invention. A preferred dosage unit may contain 1-20 mg of the stable and polymorphically pure form of monoclinic asenapine maleate of the invention.

The pharmaceutical compositions of this invention may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of the present invention may contain, in addition to the asenapine maleate of the invention, one or more additional active pharmaceutical ingredients known to be efficacious in the treatment or prevention of the conditions indicated herein, or in the treatment of co-morbidities of those conditions.

The present invention also provides a monoclinic crystalline form of asenapine maleate as defined above, or a pharmaceutical composition as defined above, for use in therapy.

Also provided is a monoclinic crystalline form of asenapine maleate as defined above, or a pharmaceutical composition as defined above, for use in the treatment or prevention of mental disorders such as bipolar disorders, psychosis, or schizophrenia.

In addition, the present invention provides a method of treatment or prevention of a mental disorder, such as bipolar disorders, psychosis, or schizophrenia, the method comprising the administration, to a subject in need of such treatment or prevention, of a monoclinic crystal form of asenapine maleate as defined above, or a pharmaceutical composition as defined above.

In another aspect, the invention provides the use of the monoclinic crystal form of asenapine maleate of the invention for the preparation of a medicament for the treatment or prevention of mental disorders, such as bipolar disorders, psychosis, or schizophrenia.

In the following, the present invention is further illustrated by the following, non-limiting examples, with reference to the enclosed figures.

EXAMPLES

General Methods

Powder X-Ray Diffraction (PXRD) patterns were acquired on a D8 Advance Series 2Theta/Theta powder diffraction system using CuKα-radiation in transmission geometry. The system was equipped with a VĂNTEC-1 single photon counting PSD, a Germanium monochromator, a ninety positions auto changer sample stage, fixed divergence slits and radial soller. Programs used: Data collection with DIFFRAC plus XRD Commander V.2.5.1 and evaluation with EVA V.12.0. The samples were prepared and placed in standard sample holders using two foils of polyacetate. Five hours scans in a range from 8° to 20° in 2θ were carried out.

Differential Scanning calorimetry (DSC) analyses were recorded in a Mettler Toledo DSC822e calorimeter. Experimental conditions: 40 μm aluminium crucibles were used; dry nitrogen atmosphere having a flow rate of 50 mL/min; heating rate of 10° C./min between 30 and 300° C. Data collection and evaluation was carried out using STARe software. The calorimeter was calibrated with indium of 99.99% purity prior and after DSC analysis.

Thermogravimetric (TGA) analyses were recorded in a Mettler Toledo SDTA851e thermobalance. Experimental conditions: 40 μm aluminium crucibles were used; dry nitrogen atmosphere having a flow rate of 80 mL/min; heating rate of 10° C./min between 30 and 300° C. Data collection and evaluation was carried out using STARe software.

Laser Diffraction Spectrometry (LDS) was used to determine the Particle Size Distribution (PSD). The samples were prepared by mixing 100 mg of asenapine maleate with 5 mL of heptane that contains 0.2% of Span-20. Ultrasonic treatment of the samples was performed for 5 minutes and the PSD was analysed using a particle size analyzer Malvern Mastersizer 2000. Refractive index of asenapine 1.800 and absorption 0.01.

Proton Nuclear Magnetic Resonance ($^1$H-NMR) analyses were recorded in deuterated methanol ($CH_3OH$-d4) in a Bruker Avance 400 Ultrashield NMR spectrometer, equipped with a z-gradient 5 mm BBO (Broadband Observe) probe with ATM and an automatic BACS-120 autosampler. Spectra were acquired solving 2-5 mg of sample in 0.7 mL of deuterated solvent.

Optical microscope. The micro photographs were obtained using a Canon Power Shot G5 digital camera attached to a Zeiss Stemi SV 11 stereomicroscope. The stereomicroscope has a variable amplification in the range between 15× and 154× and is equipped with cross coupled polarization filters (Carl Zeiss Pol 455170 and 455174) and a lambda/2 filter (Carl Zeiss Lambda 455172). For sample illumination a transmission cold light source Zeiss KL2500 LCD was used. The size of the crystals was measured using a standard microscale (5+100/100 mm, Carl Zeiss 474026).

Example 1

Preparation of Asenapine Maleate Monoclinic Form from Asenapine Maleate Monoclinic Form Having a Particle Size Distribution (PSD) Characterized by a d90 of 128 μm 4.01 g of asenapine maleate monoclinic form (1 mmol) having a PSD characterized by a d90 of 128 μm were suspended in 15 mL of methyl tert-butyl ether and stirred at room temperature for 6 hours. The resulting solid was filtered off, washed with methyl tert-butyl ether (6 mL) and dried under vacuum (3 mbar) at 45° C. for 4 hours. 3.96 g of white solid was obtained (yield: 99%). PXRD of the obtained white solid corresponded to monoclinic form, not detecting orthorhombic form. No weight loss occurred at temperatures below decomposition (below 150° C.) as demonstrated by TGA analysis. Particle Size Distribution (PSD) plot showed a monomodal curve characterized by a d90 of 16 μm.

DSC: 147° C. (75 J/g)
PSD: d95 of 24 μm

Example 2

Preparation of Asenapine Maleate Monoclinic Form from Asenapine Maleate Monoclinic Form Having a PSD Characterized by a d90 of 784 μm 4.00 g of asenapine maleate monoclinic form (1 mmol) having a PSD characterized by a d90 of 784 μm were suspended in 17 mL of methyl tert-butyl ether and stirred at 50° C. for 6 hours. The resulting solid was filtered off, washed with methyl tert-butyl ether (4 mL) and dried under vacuum (3 mbar) at 45° C. for 2 hours. 3.97 g (yield: 99%) of a white solid was obtained having a PSD characterized by a d90 of 15 μm (monomodal curve). The PXRD pattern of the white solid obtained corresponded to monoclinic form, not detecting orthorhombic form. As described under example 1, no weight loss occurred at temperatures below decomposition.
DSC: 147° C. (79 J/g)
PSD: d95 of 20 μm Example 3

Figure 4:
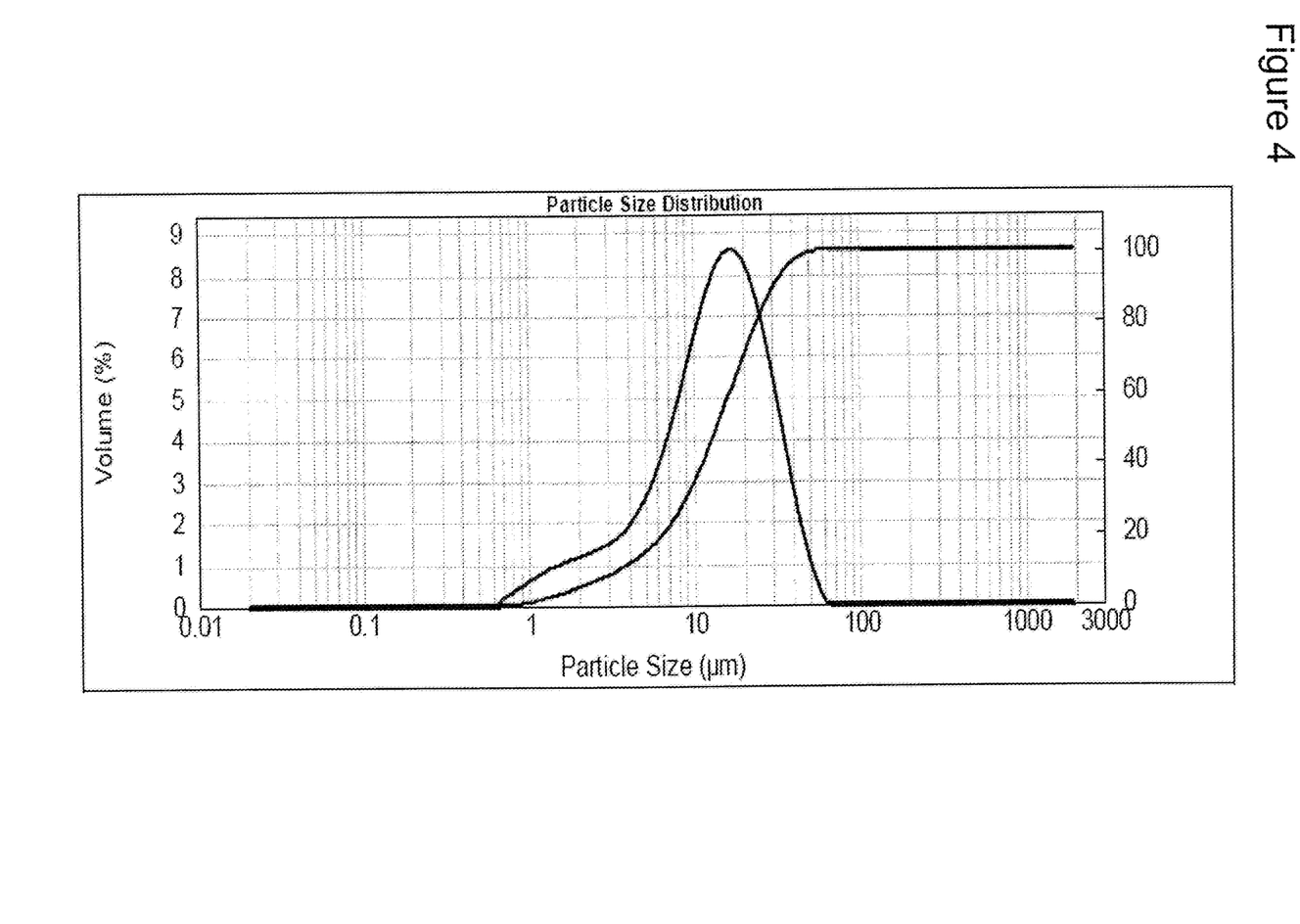
FIG. 4 shows the particle size distribution (PSD) pattern of the monoclinic crystalline form of asenapine maleate of low particle size, obtained by way of Example 3.

Preparation of Asenapine Maleate Monoclinic Form from a Heterogenic Mixture of Solids of Asenapine Maleate Monoclinic Form, which Includes Solids Having a PSD Characterized by d90 Values Between 134 and 280 μm 5.06 g of a heterogenic mixture of solids of asenapine maleate monoclinic form (1.26 mmol), which includes solids having a PSD characterized by d90 values between 134 and 280 μm were suspended in 10 mL of diisopropyl ether and stirred at 50° C. for 2 hours. The resulting solid was filtered off, washed with diisopropyl ether (3 mL) and dried under vacuum (3 mbar) at 45° C. for 2 hours. 5.06 g (yield: 100%) of a white solid was obtained having a PSD characterized by a d90 of 31 μm (monomodal curve) (FIG. 4). The PXRD pattern of the white solid obtained corresponded to monoclinic form, not detecting orthorhombic form (FIG. 1). As described under example 1, no weight loss occurred at temperatures below decomposition.
DSC: 147° C. (76 J/g) (FIG. 2)
PSD: d95 of 37 μm Example 4

Preparation of Asenapine Maleate Monoclinic Form from Asenapine Maleate Monoclinic Form Having a PSD Characterized by a d90 of 302 μm 5.19 g of monoclinic asenapine maleate (1.29 mmol) having a PSD characterized by a d90 of 302 μm were suspended in 15 mL of diisopropyl ether and stirred at 50° C. for 2 hours. The resulting solid was filtered off, washed with diisopropyl ether (4 mL) and dried under vacuum (3 mbar) at 40° C. for 17 hours. 5.17 g (yield: 100%) of a white solid was obtained having a PSD characterized by a d90 of 21 μm (monomodal curve). The PXRD pattern of the white solid obtained corresponded to monoclinic form, not detecting orthorhombic form. As described under example 1, no weight loss occurred at temperatures below decomposition.
DSC: 145° C. (75 J/g)
PSD: d95 of 28 μm Example 5

Preparation of Asenapine Maleate Monoclinic Form from Asenapine Maleate Monoclinic Form Having a PSD Characterized by a d90 of 72 μm 6.04 g of monoclinic asenapine maleate (15 mmol) having a PSD characterized by a d90 of 72 μm were suspended in 30 mL of toluene and stirred (150 rpm using an overhead U-shape stirrer) at room temperature for 20 hours. The resulting suspension was filtered off, washed with toluene (5 mL) and dried under vacuum (2 mbar) at 45° C. for 4 hours. 5.89 g (yield: 97%) of a white solid was obtained having a PSD characterized by a d90 of 29 μm (monomodal curve). The PXRD pattern of the white solid obtained corresponded to monoclinic form, not detecting orthorhombic form. PSD: d95 of 35 μm Example 6

Preparation of Asenapine Maleate Monoclinic Form by Crystallization in Presence of Cremophor RH40

7.2 g of asenapine maleate (17.9 mmol) and 2.5% (w/w) of Cremophor RH40 were dissolved in 36 mL of absolute ethanol at the reflux temperature of the solvent. The solution obtained was stirred (150 rpm using an overhead U-shape stirrer) at this temperature for 15 minutes, followed by cooling to 10° C. at a cooling rate of 3° C./min. During the cooling process, the solution is seeded with asenapine maleate monoclinic form (0.5% (w/w)) when a temperature of 30° C. was reached. After cooling to 10° C., the solution was further cooled to 0° C. at a cooling rate of 1° C./min, and stirred at this temperature for 1 hour. The suspension obtained was filtered, washed with cold absolute ethanol (5 mL) and dried under vacuum (2 mbar) at 45° C. for 4 hours. 6.12 g (yield: 85%) of a solid, with a PXRD pattern that corresponds to monoclinic form was obtained. PSD is characterized by a d90 of 46 μm and a d95 of 56 μm Example 7

Preparation of Asenapine Maleate Monoclinic Form Having a PSD Characterized by a d90 of 36 μm 3 g of monoclinic asenapine maleate (7.46 mmol), obtained as described in Example 6, were suspended in 15 mL of toluene and stirred (150 rpm using an overhead U-shape stirrer) at room temperature for 20 hours. The resulting suspension was filtered off, washed with toluene (5 mL) and dried under vacuum (2 mbar) at 45° C. for 4 hours. 2.91 g (yield: 97%) of a solid was obtained having a PSD characterized by a d90 of 36 μm. The solid obtained contained no Cremophor RH140 detected by 1H-NMR and showed a PXRD pattern that corresponded to monoclinic form, not detecting orthorhombic form.
DSC: 146° C.
PSD: d95 of 48 μm Example 8

Preparation of Asenapine Maleate Monoclinic Form by Crystallization in Presence of Tween 80

7.2 g of asenapine maleate (17.9 mmol) and 2.5% (w/w) of Tween 80 were dissolved in 36 mL of absolute ethanol at the reflux temperature of the solvent. The solution obtained was stirred (150 rpm using an overhead U-shape stirrer) at this temperature for 15 minutes, followed by cooling to 10° C. at a cooling rate of 3° C./min. During the cooling process, the solution is seeded with asenapine maleate monoclinic form (0.5% (w/w)) when a temperature of 30° C. was reached. After cooling to 10° C., the solution was further cooled to 0° C. at a cooling rate of 1° C./min, and stirred at this temperature for 1 hour. The suspension obtained was filtered, washed with cold absolute ethanol (5 mL) and dried under vacuum (2 mbar) at 45° C. for 4 hours. 6.19 g (yield: 86%) of a solid, with a PXRD pattern that corresponds to monoclinic form was obtained. PSD is characterized by a d90 of 54 μm and a d95 of 68 μm.

Example 9

Preparation of Asenapine Maleate Monoclinic Form Having a PSD Characterized by a d90 of 23 μm 3 g of monoclinic asenapine maleate (7.46 mmol), obtained as described in example 8, were suspended in 15 mL of toluene and stirred (150 rpm using an overhead U-shape stirrer) at room temperature for 20 hours. The resulting suspension was filtered off, washed with toluene (5 mL) and dried under vacuum (2 mbar) at 45° C. for 4 hours. 2.94 g (yield: 98%) of a solid was obtained, having a PSD characterized by a d90 of 23 μm (monomodal curve). The solid obtained contained no Tween 80 detected by 1H-NMR and showed a PXRD pattern that corresponded to monoclinic form, not detecting orthorhombic form.

DSC: 147° C.

PSD: d95 of 28 μm

Example 10

Preparation of Asenapine Maleate Monoclinic Form in Presence of Tween 80

14.4 g of asenapine maleate (35.8 mmol) and 2.5% (w/w) of Tween 80 were dissolved in 36 mL of absolute ethanol at the reflux temperature of the solvent. The solution obtained was stirred (150 rpm using an overhead U-shape stirrer) at this temperature for 15 minutes, followed by cooling to 10° C. at a cooling rate of 3° C./min. During the cooling process, the solution is seeded with asenapine maleate monoclinic form (0.5% (w/w)) when a temperature of 30° C. was reached. After cooling to 10° C., the solution was further cooled to 0° C. at a cooling rate of 1° C./min, and stirred at this temperature for 1 hour. The suspension obtained was filtered, washed with cold absolute ethanol (5 mL) and dried under vacuum (2 mbar) at 45° C. for 4 hours. 12.96 g (yield: 90%) of a solid, with a PXRD pattern that corresponds to monoclinic form was obtained. PSD is characterized by a d90 of 37 μm and a d95 of 49 μm.

Example 11

Preparation of Asenapine Maleate Monoclinic Form Having a PSD Characterized by a d90 of 17 μm 3 g of monoclinic asenapine maleate (7.46 mmol), obtained as described in example 10, were suspended in 15 mL of toluene and stirred (150 rpm using an overhead U-shape stirrer) at room temperature for 20 hours. The resulting suspension was filtered off, washed with toluene (5 mL) and dried under vacuum (2 mbar) at 45° C. for 4 hours. 2.94 g (yield: 98%) of a solid was obtained having a PSD characterized by a d90 of 17 μm (monomodal curve). The solid obtained contained no Tween 80 detected by 1H-NMR and showed a PXRD pattern that corresponded to monoclinic form, not detecting orthorhombic form.

DSC: 147° C.

PSD: d95 of 21 μm

Example 12

Preparation of Asenapine Maleate Monoclinic Form by Crystallization in Presence of Glyceryl Monostearate 7.2 g of asenapine maleate (17.9 mmol) and 2.5% (w/w) of glyceryl monostearate were dissolved in 36 mL of absolute ethanol at the reflux temperature of the solvent. The solution obtained was stirred (150 rpm using an overhead U-shape stirrer) at this temperature for 15 minutes, followed by cooling to 10° C. at a cooling rate of 3° C./min. During the cooling process, the solution is seeded with asenapine maleate monoclinic form (0.5% (w/w)) when a temperature of 30° C. was reached. After cooling to 10° C., the solution was further cooled to 0° C. at a cooling rate of 1° C./min, and stirred at this temperature for 1 hour. The suspension obtained was filtered, washed with cold absolute ethanol (5 mL) and dried under vacuum (2 mbar) at 45° C. for 4 hours. 6.26 g (yield: 87%) of a solid, with a PXRD pattern that corresponds to monoclinic form was obtained. PSD is characterized by a d90 of 53 μm and a d95 of 120 μm.

Example 13

Preparation of Asenapine Maleate Monoclinic Form Having a PSD Characterized by a d90 of 31 μm 3 g of monoclinic asenapine maleate (7.46 mmol), obtained as described in example 12, were suspended in 15 mL of toluene and stirred (150 rpm using an overhead U-shape stirrer) at room temperature for 20 hours. The resulting suspension was filtered off, washed with toluene (5 mL) and dried under vacuum (2 mbar) at 45° C. for 4 hours. 2.88 g (yield: 96%) of a solid was obtained having a PSD characterized by a d90 of 31 μm (monomodal curve). The solid obtained contained no glyceryl monostearate detected by 1H-NMR and showed a PXRD pattern that corresponded to monoclinic form, not detecting orthorhombic form.

DSC: 147° C.

PSD: d95 of 38 μm

The invention claimed is:

1. A monoclinic crystalline form of asenapine maleate characterized in that it is not micronized, has a polymorphic purity of more than 90%, and has a particle size distribution characterized by a d90 of 31 μm or less, preferably of 16 μm or less.

2. A monoclinic crystalline form of asenapine maleate according to claim 1 with a polymorphic purity of more than 95%.

3. A process for the preparation of a monoclinic crystalline form of asenapine maleate, the process comprising the following steps:
   a) providing a mixture of monoclinic asenapine maleate and an organic solvent which, under the conditions of the process, acts as an antisolvent;
   b) stirring the mixture at a temperature between 15 and 60° C.; and
   c) collecting the crystals,
wherein the organic solvent is selected from alcohols, ketones, ethers, esters, hydrocarbons or mixtures thereof.

4. A process according to claim 3, wherein the organic solvent is selected from methyl tert-butyl ether, diisopropyl ether, methyl ethyl ketone, methyl isobutyl ketone, isopropyl acetate or toluene.

5. A process according to claim 3, wherein the mixture is stirred at a temperature of between 25 and 50° C.

6. A process according to claim 3, wherein the particle size distribution of the monoclinic crystalline form of asenapine maleate produced by the process is characterized by a d90 of 40 μm or less.

7. A process according to claim 3, wherein the particle size distribution of the monoclinic crystalline form of asenapine maleate produced by the process is characterized by a d95 of 40 μm or less, preferably of 30 μm or less.

8. A process according to claim 3, wherein the monoclinic crystalline form of asenapine maleate has a polymorphic purity of more than 90%, preferably more than 95%.

9. A process according to claim 3, wherein the monoclinic asenapine maleate of step (a) is obtained by a process comprising: dissolving a mixture of asenapine maleate and a surfactant in ethanol at reflux temperature; cooling the solution obtained to about 0° C. under conditions of controlled cooling; optionally seeding the solution with asenapine maleate monoclinic crystals; and collecting the crystals of monoclinic asenapine maleate which crystalise from the solution.

10. The process of claim 9, wherein the solution is cooled at a rate of about 3° C. per minute until a temperature about 10° C. is reached; followed by a second controlled rate of about 1° C. per minute until a temperature about 0° C. is reached.

11. A monoclinic crystalline form of asenapine maleate which has a melting point in the range of 142° C. - 147° C., obtained or obtainable by the process of claim 3.

12. A pharmaceutical composition comprising a monoclinic crystalline form of asenapine maleate according to claim 1, and one or more pharmaceutically acceptable excipients.

13. A method of treatment of bipolar disorders, psychosis, or schizophrenia, the method comprising the administration, to a subject in need of such treatment, of a monoclinic crystalline form of asenapine maleate according to claim 1.

14. A pharmaceutical composition according to claim 12, containing one or more additional, pharmacologically active ingredients.

15. A pharmaceutical composition comprising a monoclinic crystalline form of asenapine maleate according to claim 11, and one or more pharmaceutically acceptable excipients.

16. A method of treatment of bipolar disorders, psychosis, or schizophrenia, the method comprising the administration, to a subject in need of such treatment, of a pharmaceutical composition according to claim 12.

* * * * *